United States Patent [19]
Fukushima et al.

[11] Patent Number: 6,123,661
[45] Date of Patent: Sep. 26, 2000

[54] RELAX REFRESH SYSTEM

[75] Inventors: Shogo Fukushima; Kenshi Suzuki, both of Kadoma, Japan

[73] Assignee: Matsushita Electric Works, Ltd., Osaka, Japan

[21] Appl. No.: 08/842,037

[22] Filed: Apr. 23, 1997

[30] Foreign Application Priority Data

May 28, 1996 [JP] Japan .................................. 8-133064
May 28, 1996 [JP] Japan .................................. 8-133070
Oct. 28, 1996 [JP] Japan .................................. 8-284896

[51] Int. Cl.$^7$ .................................................. A61M 21/00
[52] U.S. Cl. .............................................. 600/27; 600/26
[58] Field of Search .......................... 600/26, 27; 463/31, 463/32; 434/236, 237, 238, 308, 310, 314

[56] References Cited

U.S. PATENT DOCUMENTS 5,304,112  4/1994  Mrklas et al. .
5,846,134  12/1998  Latypov ..................................... 463/46

Primary Examiner—Linda C. M. Dvorak
Assistant Examiner—Rosiland Kearney
Attorney, Agent, or Firm—Burns, Doane, Swecker & Mathis, L.L.P.

[57] ABSTRACT

A relax refresh system is arranged such that a system control section performs a control of having a moving image track reproduced by a video CD driving section through an image/sound control section, the track including a modem signal recorded in a voice zone, control data are decoded by a modem signal decoding section from a code of the modem signal, the decoded control data are sent to the system control section, the video CD driving section is controlled through the image/sound control section by the system control section so as to reproduce the moving picture track, and the video CD driving section and a display device are controlled in their operation by means of data groups of the moving picture track preliminarily read in the system control section, in synchronism with the moving image track being reproduced, whereby the image and voice in accordance with a state of the user can be sufficiently provided to the user.

5 Claims, 8 Drawing Sheets

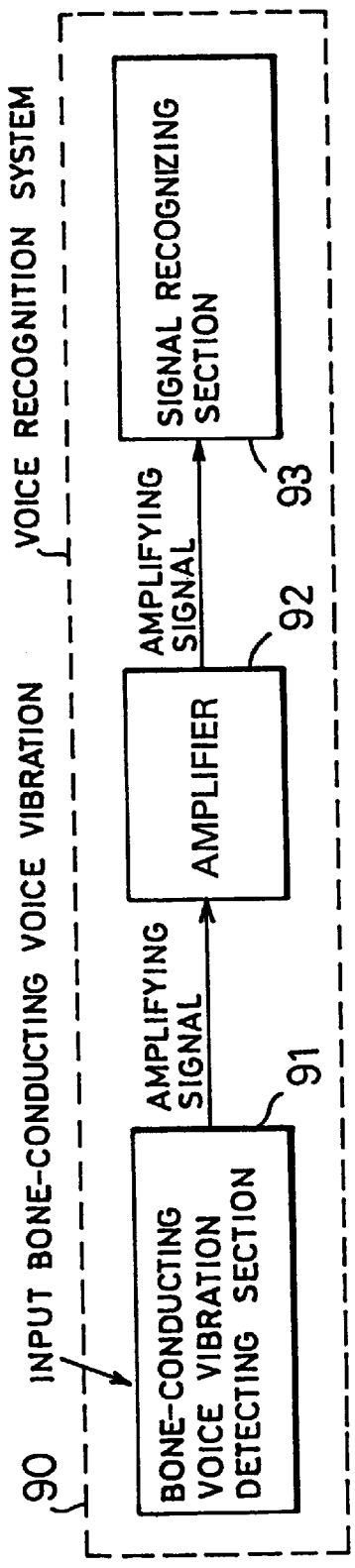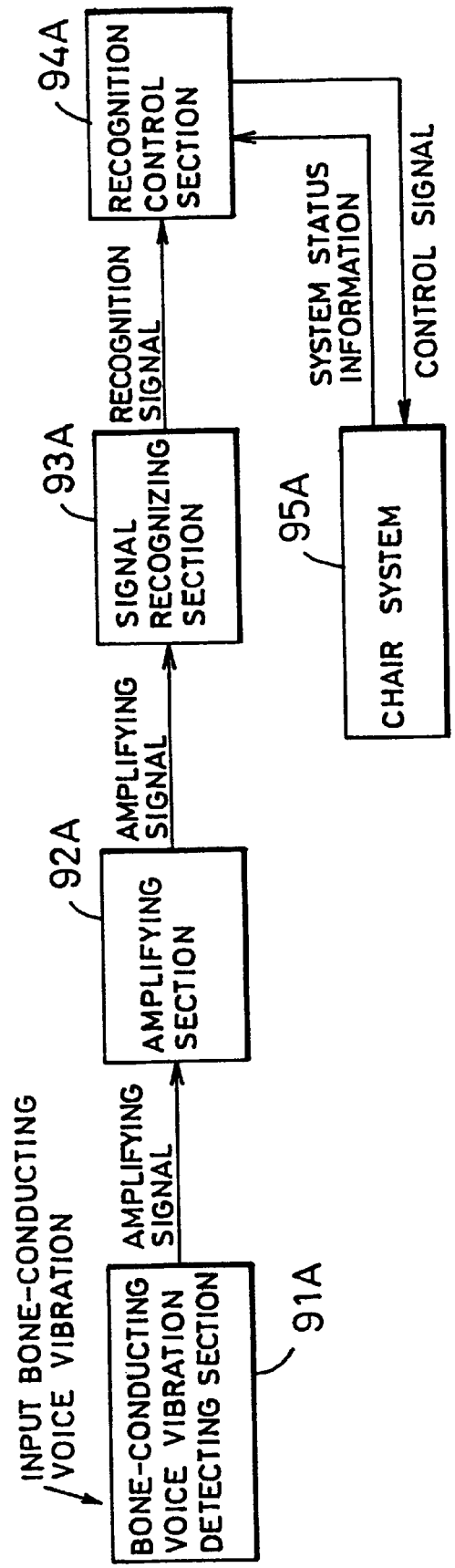

FIG. 10A

PICTURE OF COURSE SELECTION MENU:

PLEASE TELL DESIRED
COURSE NUMBER.
IF THE NUMBER IS CORRECT,
PLEASE TELL "DEFINITE".

1. MIDSUMMER SUN
2. MORNING GLOW

FIG. 10B

PICTURE OF TIME SELECTION MENU:

PLEASE TELL NUMBER
OF DESIRED TIME.
IF THE NUMBER IS CORRECT,
PLEASE TELL "START."

1. 10 MINUTES
2. 15 MINUTES

RELAX REFRESH SYSTEM

BACKGROUND OF THE INVENTION

This invention relates to a relax refresh system for giving to a user a sense of relax and refresh with images reproduced in front of eyes of the user by means of a display device mounted to the head of the user.

DESCRIPTION OF RELATED ART

In such known systems employing images and voice (sound of music, narration or their combination) as those disclosed in U.S. Pat. No. 5,304,112 to MrKlas et al. and Japanese Patent Laid-Open Publication No. 6-225941, it has been attempted to lead the user quickly to a relaxed state in accordance with a degree of relax of the user by means of the image, voice, massager movement and their combination, and also to have the user refreshed. In the latter Japanese publication, in particular, a video tape is employed as a recording medium of image signals and voice signals, the voice signals of the music, narration and so on corresponding to the images recorded on an image track are recorded on one of voice tracks provided on both side zones of the video tape, and control data for controlling the operation of a massager with DTMF signals employed for dial calling in key-telephones as well as further control data for ON/OFF control of reproduction of the image and voice signals are recorded on the other voice track in correspondence to recorded position of the image and voice signals with which the control signals are intended to be synchronized.

In order to provide to the user a feeling of reality, further, an image reproducing means employs an image reproducing section in a head-mounted display device, the user mounts the video tape in a video amplifier available in the market, first, and the head-mounted display device on the head, and the video amplifier is caused to be operated for the reproduction by means of a remote controller, to have the system started in its operation of the whole function, after sitting on a chair in the event where the system is one employing a chair-type massager.

In the foregoing known art, however, there has been a problem that, in respect of the image and voice, the control has been enabled only in turning ON or OFF their reproduction in accordance with the user's demand but has been difficult to sufficiently provide the image and voice in response to the state of the user.

In the foregoing known art, further, there has been a problem that the system is not excellent in the usability and is uneasy to control the video tape mounted in the video amplifier, due to the mounting of the head-mounted display device, specifically when the user intends to perform such action as the starting, interruption, stopping and so on.

Further, in the use of the head-mounted display device in the system for the purpose of attaining the relaxation, it has been another problem that a state in which the head-mounted display device is kept connected to the power source even when the user is in sleeping state.

In the foregoing known art, there has been still another problem that, as the DTMF signals of analog signal in audible range are used as the signals for controlling the reproduction of the massage action, image signals and voice signals and required recording time for the DTMF signals has been prolonged, the signals have had to occupy the whole of the voice track on one side zone of the video tape and, consequently, the voice of this video tape has been forced to be monophonic.

An object of the present invention is to provide a relax refresh system which can overcome the foregoing problems and is capable of sufficiently providing the images and voice (sound) to the user in accordance with the state of the user.

According to the present invention, the above object can be realized by means of a relax refresh system comprising means for detecting physiological state of the user; an image reproducing means; a sound reproducing means; a recording medium including recording zones respectively for recording at least image signals and voice signals in a manner of allowing them reproduced through a random access; a recording medium driving means for driving the medium to reproduce the recorded signals; and a control section at least comprised of a first control means for controlling the recording medium driving means so as to modify reproducing position on the recording medium to meet an operation course preliminarily selected in view of the state of the user grasped on the basis of a detection signal of the physiological state detecting means, and for reproducing at the image reproducing means and sound reproducing means the image signals and voice signals output from the recording medium driving means, and a second control means for generating voice signals of a narration along an operation course preliminarily selected in view of the state of the user grasped on the basis of the detection signal of the detection means and for reproducing at the sound reproducing means the voice signals of the narration.

Other objects and advantages of the present invention shall become clear as the description of the invention advances in the followings as detailed with reference to embodiments shown in accompanying drawings.

BRIEF EXPLANATION OF THE DRAWINGS

FIG. 7 is a block diagram of a circuit employed in the embodiment of FIG. 6;

FIG. 9 is a block diagram of a circuit employed in the embodiment of FIG. 8;

FIGS. 10A and 10B are diagrams showing course and time selection menus in pictures employed in the display device of the present invention.

Figure 1:
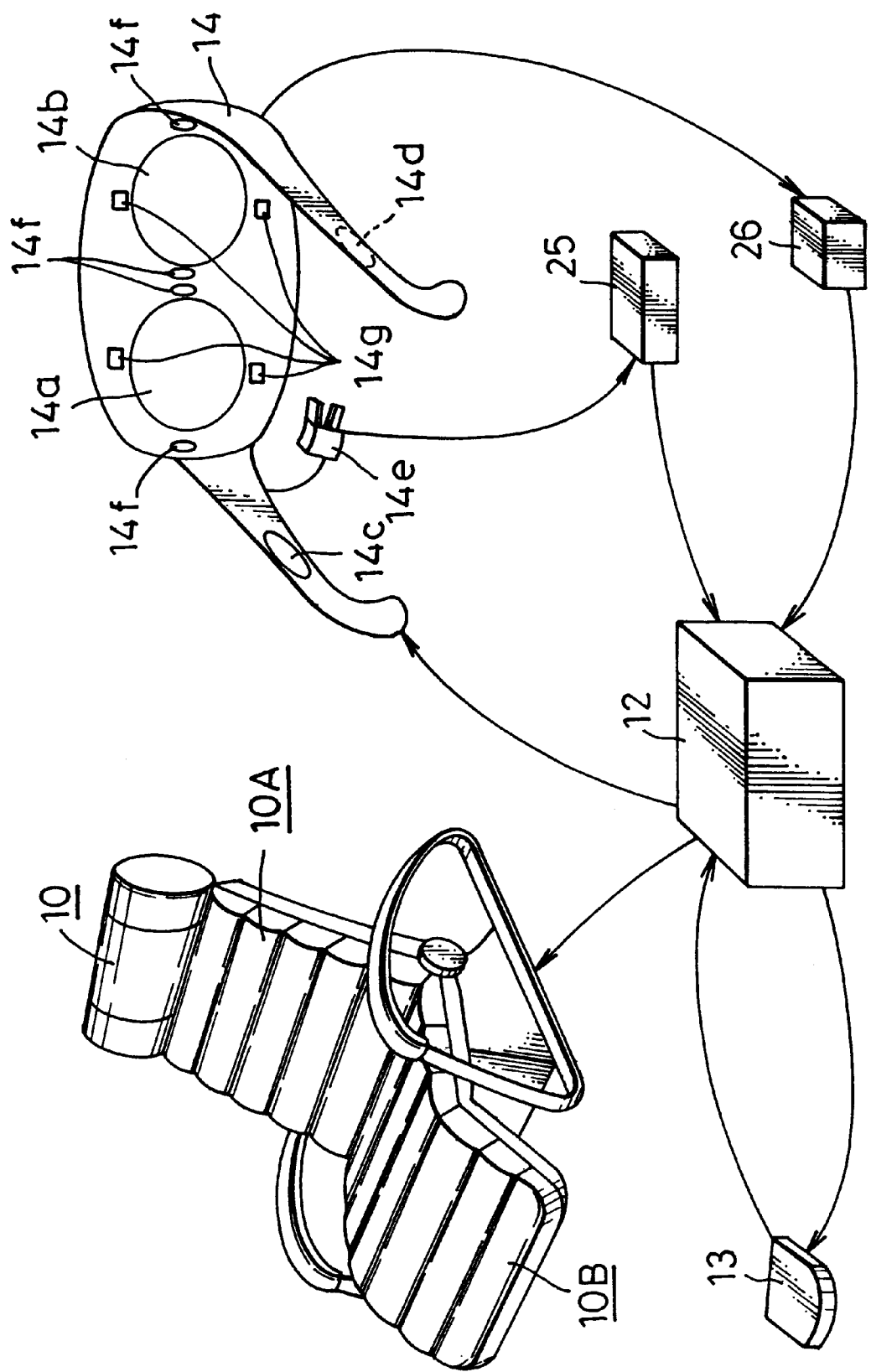
FIG. 1 is a schematic perspective view showing the relax refresh system according to the present invention.

It should be appreciated that, while the present invention shall now be described with reference to the embodiments shown in the drawings, the intention is not to limit the invention only to these embodiments but rather to include all altrations, modifications and equivalent arrangements possible within the scope of appended claims.

DETAILED DESCRIPTION OF THE PREFERRED EMBODIMENTS

Figure 2:
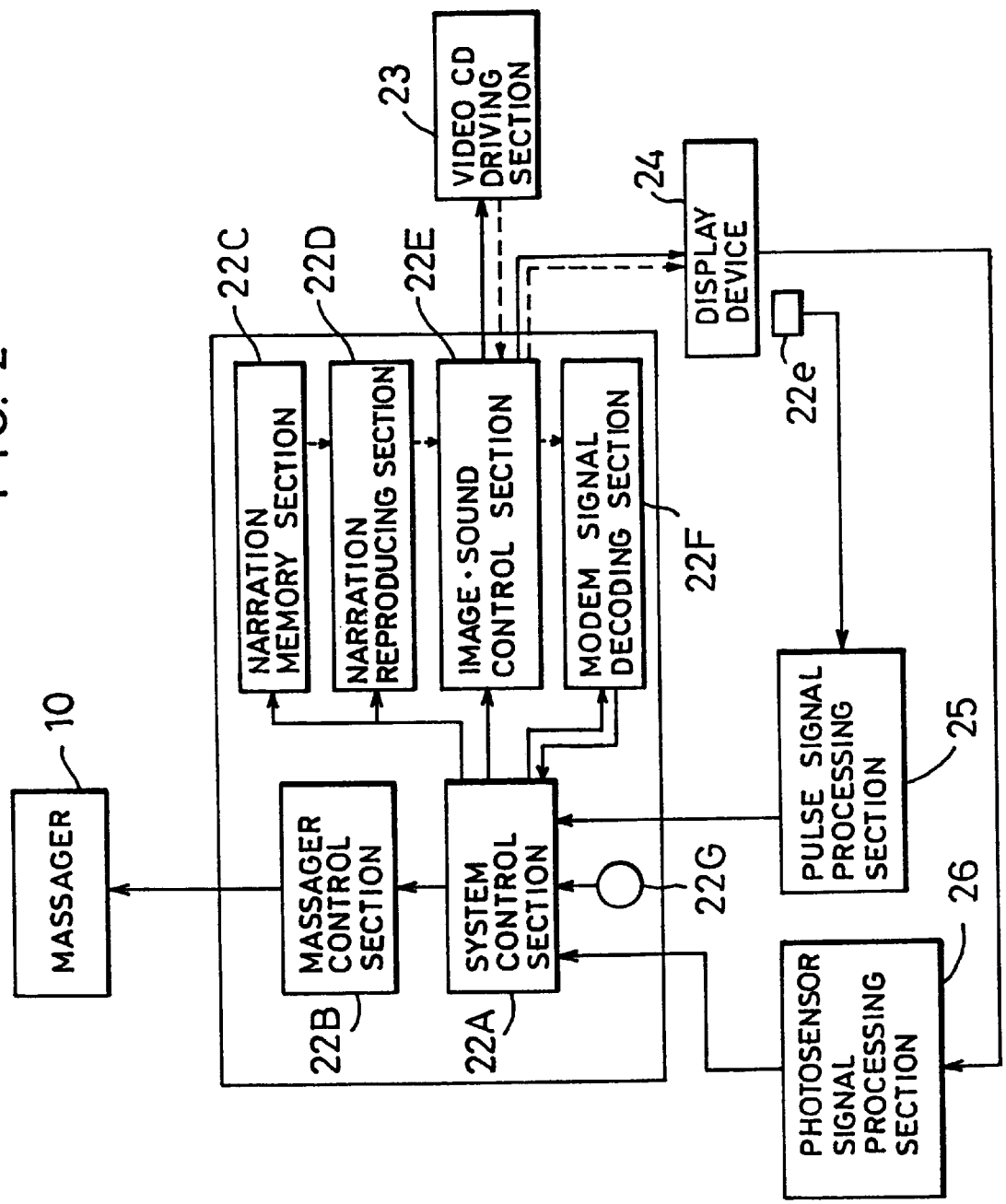
FIG. 2 is a circuitry block diagram of a circuit employed in the relax refresh system of FIG. 1.

In FIG. 1, an entire arrangement of the relax refresh system in an embodiment of the present invention is shown, and FIG. 2 shows a general circuit of the arrangement. The present embodiment is of an aspect in which a massager 10 is concurrently used, which massager 10 is of a chair-type. A reclining mechanism (not shown) for varying angle of inclination of the back 10A and foot-rest 10B and a vibration mechanism (not shown) for giving to the user body a vibration are incorporated inside the back 10A and foot-rest 10B. These reclining and vibration mechanism are controlled by control signals provided from a massager control section 22B of a controller 12, and the operation of this massager control section 22B can be contolled by a system control section 22A which controls the entirety of the system.

On the other hand, a sound reproducing means and an image reproducing means are provided integral with a head-mounted display device 14 formed in an aspect of eyeglasses, and the image reproducing means is constituted by image display sections 14a and 14b respectively comprising liquid crystal displays corresponding to the user's left and right eyes, which sections 14a and 14b being provided for receiving through the controller 12 composite image signals from a video CD driving section 13, and displaying the image on the image display sections 14a and 14b. Further, the sound reproducing means comprises headphones 14c and 14d provided in both side bows to be hung on ears of the user, so that voice signals of music or the like from a video CD driving section 23 as well as reproduced voice signals of a required narration selected from several types of stored narrations in a narration memory section 22C under the control of the system control section 22A and reproduced at a narration reproducing section 22D will be received through the controller 12 by the headphones 14c and 14d to be reproduced there.

Further, at the video CD driving section 23, PBC function and reproduced track change of the video CD are controlled by means of a control signal from an image/sound control section 22E and, at the display device 14, receiving control of the composite signals and voice signals as well as ON/OFF and fade-in/fade-out controls of the image display sections 14a and 14b are carried out. These narration memory section 22C, narration reproduction section 22D and image/sound control section 22E are controlled by the system control section 22A.

Here, the video CD of existing format is employed as the recording medium of the image and sound in the present embodiment, and such five different groups of data as follows in respective moving image tracks, for example, are recorded by means of such modem signal as analog signal of audible band in a voice range of a certain moving image track (based on such standard as CCITT V.23):

(1) Attribute allocation data depending on the type of image and sound;
(2) continued time data;
(3) control data for controlling the operation of the video CD driving section 23 (shift to a next reproduced track);
(4) control data for controlling the operation of the head-mounted display device 14 (ON/OFF and fade-in/fade-out control of the image displaying sections 14a and 14b and headphones 14c and 14d as well as receiving control of the composite signals and voice signals); and
(5) further control data, in case of concurrently employing the massager 10, for controlling the operation of the massager 10 (such massager operation for every track as shown in a following Table 1).

More specifically, there are provided in moving image tracks, for example, in the video CD, operation tracks of such state as mentally relaxed and refreshed states and sleeping state, other than the foregoing system controlling tracks, which will be in concrete such operation tracks as in A to F of the following Table 1;

TABLE 1

| Track No. | Image | *Music *Narration | Op. of Massager 10 (vib.Mech.of 10A&10B) (Recl.Ang.of 10A&10B) | Pattern Class. |
|---|---|---|---|---|
| A | Calm Rural Scene | *Mentally Calming Music *You'll be calmed mentally & physically. | Op. of Relaxed St. (Peaceful Vib. eg. faint vib. of l/f fluctuation) (45°) | Mentally Relaxed St. Attained. |
| B | Morning Glow | *Energetic Musc. *Now it's morning. Let's wake up. | Op. of Refreshed St. (Strong, energetic vibration) (90°) | Mentally Refreshed St. Attnd. |
| C | (Nil) | *Drowsy Music *(Nil.) | Op. of Sleeping St. (Peaceful Vib. eg. faint vib of l/f fluc.) (30°) | Sleeping St. Attained. |
| D | Evening Glow | *Mentally Calming. Music *You'll become steadily sleepy. | Op. of Relaxed St. (Peaceful vib. eg. Faint Vib. of l/f Fluc.) (45°) | Mentally Relaxed St. Attained. |
| E | Helicopter Taking Off. | *Energetic Music *You'll get filled with vitality | Op. of Refreshed St. (Strong, Energetic Vib.) (90°) | Mentally Refreshed St. Attnd. |
| F | (Nil) | Modem Signals | | System Controlling Track |

The track No. F in the video CD is reproduced by the video CD driving section 23, the output modem signals are provided as an input to a modem signal decoding section 22F, and the system control section 22A controls, on the basis of control data obtained from the modem signal decoding section 22F, the massager control section 22B, narration memory section 22C, narration reproducing section 22D and image/sound control section 22E.

The display device 14 is provided with a pulse sensor 14e for obtaining physiological information of the user, pulse data detected by this sensor 14e is provided to a pulse signal processing section 25 to calculate the user's heart rate, and the resultant heart rate is sent to the system control section 22A.

Further, the display device 14 is provided with infrared ray LED's 14f and photosensors 14g, for the purpose of detecting eyeblinking or opening and closing state of the user's eyes. That is, the user's eyes are irradiated by the infrared rays by means of the infrared ray LED's 14f, reflected infrared rays from the eyes are detected by the photosensor 14g, the opening and closing (eyeblinking) of the eyes is discriminated at a photosensor signal processing section 26 with variation rate of the sensed signal of the photosensors 14g caused by the opening and closing state of eyelids, and the discrimination result is provided to the system control section 22A. Since the sensed signals of the photosensors 14g are mostly faint, the photosensor signal processing section 26 once amplifies the output signals of the photosensors 14g and thereafter discriminates the eyeblinking state in accordance with signal characteristics denoting the opening and closing state of the eyes.

The controller 12 should desirably be constituted by, in concrete, the modem signal decoding section 22F for decoding the modem signal obtained from the video CD driving section 23, the massager control section 22B for controlling the massager 10, the image/sound control section 22E for controlling the video CD driving section 23 and head-mounted display device 14, the narration memory section 22C where the necessary narration is selected from the narrations preliminarily recorded, the narration reproducing section 22D for reproducing the voice signal of the narration from the narration memory section 22C at the headphones 14c and 14d, a start button 22G for actuating the controller, and the system control section 22A where the control signals for controlling the respective sections 22B through 22E are prepared for rendering the entire system to be controllable on the basis of such data as the control data and the like obtained from the modem signal decoding section 22F, the heart rate obtained from the pulse signal processing section 25 and the information of the eyeblinking or opening and closing of the user's eyes obtained from the photosensor signal processing section 26.

In FIG. 2, a power source for the respective sections and power supply paths between them are omitted, while the flow of the voice and composite signals is shown by arrows of broken line and the flow of the control signals and data is denoted by arrows of solid lines.

The operation of the system according to the present invention shall be described next.

First, the user pushes the start button 22G provided on the controller 12 to actuate it, then mounts the head-mounted display device 14 onto the user's head and, when the massager 10 is used together, sits on the massager.

The pushed state of the start button 22G is transmitted to the system control section 22A and, on the basis of this pushed state of the start button 22G, the system control section 22A executes the control of causing, through the image/sound control section 22E, the video CD driving section 23 to reproduce the moving image track in which the modem signal is recorded in the voice range. The control data are decoded by the modem signal decoding section 22F from the code of the modem signal reproduced by this control, the decoded control data are sent to the system control section 22A, such data groups as the foregoing five different data (1) to (5) in the respective moving image tracks of all track Nos. A to E, for example, are read into the system control section immediately after the actuation of the controller, a menu picture is thereafter displayed on the image display sections 14a and 14b, and the user is allowed to perform a course selection, confirmation and start by means of preliminarily set eyeblinking patterns of both eyes.

Here, the arrangement is so made that, upon closing of the eyes for a long time, the power source of the display device 14 is turned OFF, so that the power can be saved.

When, on the other hand, the detection result obtained from the photosensor signal processing section 16 is sent to the system control section 22A and the course selected and confirmed by the user is discriminated at this section to be, for example, a relax-refresh course, this course is to initially lead the user to a relaxed state, to induce the user to sleep after a certain period for keeping the relaxed state and thereafter to lead the user to the refreshed state, which course being realized by reproducing the moving image track in the sequence of the track No. A→track No. C→track No. B. Here, after the execution of the start by the user, the system control section 22A controls through the image/sound control section 22E the video CD driving section 23 to have the moving image track reproduced in the above sequence, and the operation of the massager 10, video CD driving section 23 and display device 14 is controlled by means of the data groups of the moving image track preliminarily read in the system control section 22A, in synchronism with the moving image track being reproduced.

The massager 10 is controlled to perform such operation of the massager of each of the tracks A to F as shown in Table 1, and the video CD driving section 23 is controlled to shift its head to the moving image track to be reproduced next. To the display device 14, the image and voice signals are input, so that ON or fade-in control of the image displaying sections 14a and 14b and headphones 14c and 14d immediately after the reproduction of the track as well as OFF or fade-out control of the image display sections 14a and 14b and headphones 14c and 14d immediately before termination of the track reproduction are performed.

In this manner, the system of the present invention in this embodiment performs the program operation on the basis of the image, music, narration and control date preliminarily recorded in the video CD, and the user is led to, for example, the relaxed state, sleeping state or refreshed state.

Further, not only the above functions, but also such pulse feedback control of five cases as follows in accordance with the heart rate of the user obtained from the pulse sensor 14e and pulse signal processing section 25 will be performed. It is assumed here that, for example, the relax-refresh course in which the foregoing tracks are reproduced in the sequence of the track No. A→track No. C→track No. B is selected. In the case (1), a heart rate of the user below a predetermined level in the stage of the track A results in that the system control section 22A provides through the image/sound control section 22E to the display device 14 a control signal for stopping reception of the composite and voice signals and a fade-out control signal for the image display sections 14a and 14b and the headphones 14c and 14d. That is, it is attempted not to hinder the relaxed state of the user.

In the case (2), as the system control section 22A discriminates that the user's heart rate still does not fall in the stage of the track No. A, the system control section 22A refers to the attribute allocation data depending on the type of the image and sound of the data groups in the moving image tracks preliminarily read in the system control section 22A, provides through the image/sound control section 22E to the video CD driving section 23 a control signal for reproducing the track D determined to be better in leading to the relaxed state than the track No. A, immediately after interruption of the reproduction of the track No. A, and further provides to the display device 14 the fade-out control signal and fade-in control signal for the image display sections 14a and 14b and the headphones 14c and 14d in synchronism with track alteration during the reproduction. Further, the system control section 22A provides to the narration memory section 22C and narration reproducing section 22D a control signal for extracting and reproducing such narration suitable to this track alteration during the reproduction that "body strength is going gradually slowly". That is, the arrangement is so made as to lead the user who is not in the relaxed state to the relaxed state by means of the image, music and narration.

In the case (3), as the system control section 22A determines, in the stage of the track No. C, that the heart rate of the user is gradually lowered in the latter half of this stage and the reproduction of the next track B is too early to be started, the system control section 22A provides through the image/sound control section 22E to the video CD driving section 23 a control signal for repeating the track No. C being reproduced. That is, the arrangement is made not to hinder the sleeping state of the user.

In the case (4), as the system control section 22A determines, in the stage of the track No. C, that the heart rate of the user gradually increases in the latter half of this stage and the particular stage should not be continued but rather be shifted to another stage for attaining the refreshed state, the system control section 22A provides through the image/sound control section 22E to the video CD driving section 23 a control signal for reproducing the track B immediately after interruption of the reproduction of the track No. C, and provides to the display device 14 the fade-out control signal and fade-in control signal for the image display sections 14a and 14b and headphones 14c and 14d in synchronism with the track alteration during the reproduction. That is, the arrangement is so made as to lead the user who has awaken from sleeping to the refreshed state.

In the case (5), as the system control section 22A determines that the heart rate of the user still does not increase in the stage of the track No. B, the system control section 22A refers to the attribute allocation data depending on the type of the image and voice of the data groups in the moving image track preliminarily read in the system control section 22A, provides through the image/sound control section 22E to the video CD driving section 23 a control signal for reproducing the track No. E regarded to be better in leading the user to the refresh state than the track B immediately after interruption of the reproduction of the track No. B, and provides to the display device 14 the fade-out control signal and fade-in control signal of the image display sections 14a and 14b and headphones 14c and 14d in synchronism with the track alteration during the reproduction. Further, the system control section 22A provides to the narration memory section 22C and narration reproducing section 22D a control signal for extracting and reproducing such narration that suitable for the track alteration during the reproduction, for example, "you are getting filled with vitality". That is, the arrangement is so made that the user not in the refreshed state is led to the refreshed state by means of, in particular, the image, music and narration.

In this way, it is enabled to attain suitable state and continued eyeblinking time (time from closing to opening of eyes) to the state of individual user, through alteration of the program operation by means of the image, music, narration and control data preliminarily recorded in the video CD in accordance with the state of the heart rate of the user. Further, not only the pulse feedback control in accordance with the heart rate of the user, the respective sections 22E, 22B, 22C and 22D may also be subjected, as determined by the user during any course, to an intermediate alteration of the moving image track being reproduced with respect to the image/sound control section 22E, for example, an intermediate alteration of the operation of the massager 10 with respect to the massager control section 22B, or a generation and alteration of narration with respect to the narration memory section 22C and narration reproducing section 22D.

Further, instead of using the foregoing head-mounted display device 14, an ordinary display device may also be employed. It is also possible to perform the course selection, confirmation and start of the menu picture by means of an operating switch or the like, without using such function of detecting the eyeblinking or eye opening/closing state provided to the display device 14 as has been described. Further, as the foregoing recording medium for the image and so on, DVD or any other recording medium capable of reproducing the image and voice through random access may also be employed, other than the video CD. In such case, a reproducing device corresponding to such recording medium should of course be employed.

Figure 3:
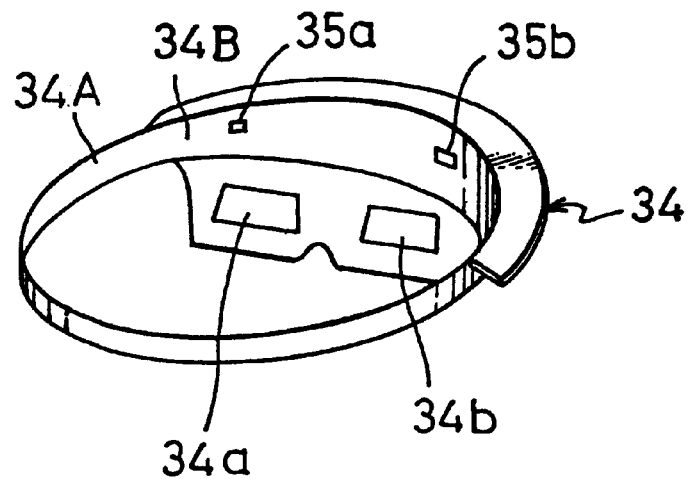
FIG. 3 is a schematic perspective view of a display device in another embodiment of the present invention.

In another embodiment shown in FIG. 3, the display device 34 comprises a mounting band 34A as means for mounting the device to the user's head, a display section 34B continuously provided to the mounting band 34A and to be positioned in front of the user's eyes, such acoustic means (not shown) as the headphone incorporated in the mounting band 34A for generating sounds, and photosensors 34a and 34b embedded in the mounting band 34A at positions contacting with the user's forehead. That is, porisions in the user's forehead to which the photosensors 34a and 34b opposes are determined by the mounting of the display device 34 to the user's head. The number of the photosensors may not be limited to be two, but may be one or three.

The display section 34B includes liquid crystal displays 35a and 35b provided to correspond to both side eyes, for displaying the images from image reproducing equipment. The image to be displayed at the display section 34B may be three dimensional or two dimensional or even both. Since required technique for displaying such image has been well known, its description shall be omitted.

Figure 4:
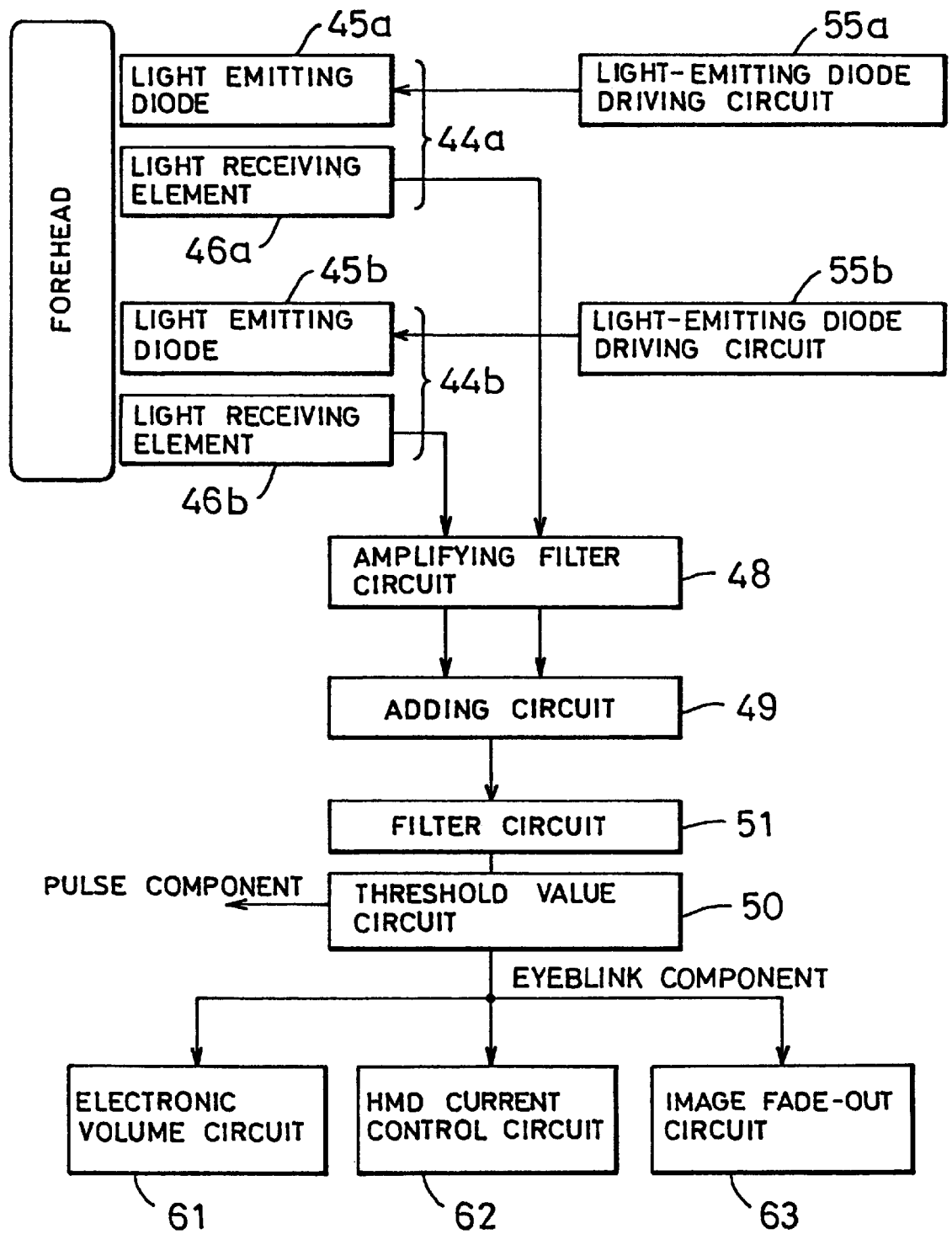
FIG. 4 is a block diagram of a circuit employed in the embodiment of FIG. 3.

In the followings, only characterizing portions of this embodiment are described with reference to FIG. 4.

The photosensors 34a and 34b comprises light emitting diodes 45a and 45b as the light emitting elements, and light receiving elements 46a and 46b, emitted light of the light emitting diodes 45a and 45b actuated by means of light-emitting diode driving circuits 55a and 55b is irradiated onto the forehead of the user, reflected light is received by the light receiving elements 46a and 46b, and signals corresponding to received amount is output.

The output signals of the photosensors 34a and 34b, that is, the output signals of the light receiving elements 46a and 46b are input to a later described signal processing means. While in this case the photosensors 34a and 34b irradiate the surface of the user's forehead by the light emitting diodes 45a and 45b and the reflected light is received by the light receiving elements 46a and 46b, the received light amount at the light receiving elements 46a and 46b, that is, the amount of the reflected light is varied as influenced by light absorbing amount of hemoglobin contained in the blood of the user, it is possible to detect variation in blood amount, that is, the pulse of the user.

The above signal processing means forms means for detecting the user's heart rate and eyeblinking on the basis of the output signals of the photosensors 34a and 34b, and comprises an amplifying filter circuit 48 for amplifying the respective output signals of the photosensors 34a and 34b separately, an adding circuit 49 for an addition of both output signals of the photosensors 34a and 34b, a filter circuit 50 forming a discriminating circuit for descriminating the output signal of the adding circuit 49 into a pulse component (pulse signal) and an eyeblinking component (eyeblinking signal), and a threshold value circuit 50 for comparing the pulse signal and eyeblinking signal from the filter circuit 51 with their predetermined threshold values and removing any noise. Accordingly, it is possible to obtain the heart rate from the pulse signal from the threshold value circuit 50 and the eyeblinking from the eyeblinking signal from th e circuit 50. When a single photosensor is employed, the adding circuit 49 is not required.

While the pulse signal detected through the photosensors 34a and 34b involves various noises superposed, the respective output signals of the photosensors 34a and 34b are added to each other in the present embodiment so that, as compared with the case of the single photosensor, the signal input to the filter circuit 51 can be improved in the S/N ratio, and demanded specification for the filter circuit 51 is made thereby lenient so as to render its design work to be easier and any electric noise filter to be unnecessary.

In the present embodiment, on the other hand, a detection of a state in which the user's eyes are closed as continued for a fixed period causes an electronic volume circuit 61 actuated to reduce the volume of reproduced voice, so that the sleeping state of the user can be prevented from being hindered. Further, the arrangement may be so made that, as the continued closed-eye state for the fixed period is detected, an electric power supply to the electronic volume circuit 61 and to an image fade-out circuit 63 will be cut by a source current control circuit 62, whereby the sleeping state of the user can be prevented from being hindered, while also attaining a saving of electric power by cutting the source.

Thus it is enabled to obtain the heart rate in easy manner of handling only by mounting the display device 34 with the mounting band 34A to the head of the user, without need of mounting any separate pulse sensor to an ear lobe or to a finger, and also enabled to detect the user's eyeblinking in the easy manner without performing any optical axis adjustment for irradiating light, so that the user can be relaxed and refreshed by varying the state of images and voice or controlling as interlinked any external equipment. Further, it is not required to directly irradiate light onto eye balls, so that it is also enabled to employ even a visible light.

In the present embodiment, further, the photosensors 34a and 34b are disposed on the mounting band 34A so as to be positioned above both eyes, so that the arrangement may be also made to provide a sign detecting means for detecting a sign by means of the eyeblinking of only one of the eyes on the basis of the mutual output signals of the photosensors 34a and 34b at the positions symmetrical, and the state of the image and voice, for example, is varied in response to the sign by means of the eyeblinking of the user, so as to control any external equipment in interlinking manner. As an example, it is possible to adjust the luminance of the liquid crystal displays 35a and 35b or to modify the volume of the headphones, in response to the sign by means of the eyeblink of right side eye.

While in the present embodiment, further, the pulse component and eyeblinking component are discriminated at the filter circuit 5 on the basis of the output signals of the photosensors 34a and 34b, it is possible to extract the eyeblinking component only while cancelling the pulse component, by disposing the photosensors 34a and 34b as vertically separated so as to oppose upper and lower parts of the forehead of the user and obtaining a difference between the output signals of both photosensors 34a and 34b. Therefore, the user can be relaxed and refreshed by varying the state of image or voice or controllably actuating the external equipment, in accordance with the eyeblinking thus detected.

The photosensor may be constituted by a pair of the light emitting elements and a pair of the light receiving elements, or even by a combination of one light emitting element with two light receiving elements.

Figure 5:
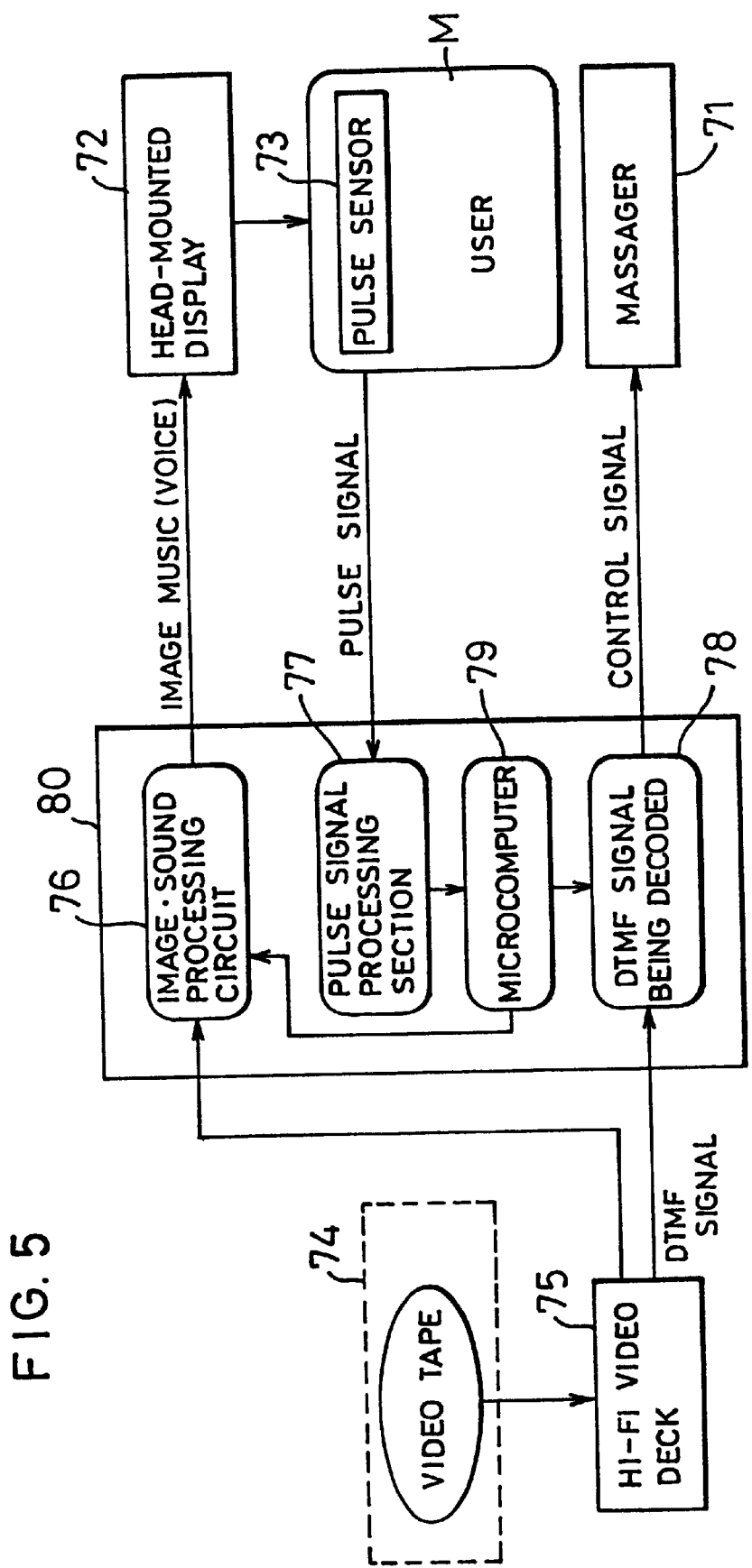
FIG. 5 is a block diagram showing schematically a circuit arrangement for use in another embodiment of the present invention.

FIG. 5 shows another embodiment of the system according to the present invention, including a storage medium, a system controller based on the medium, and a massager to be controlled. This system comprises a massager 71 for providing to the user M a variety of massaging action; a head-mounted display 72 for providing to the user M images displayed and music or narration for listening; a pulse sensor 73 for sensing such physiological signal of the user M as the pulse; a video deck 75 of high-fidelity type available in the market for reproducing, from such storage medium as an existing video tape 74 corresponding to the deck, image signals to be shown to the user M, voice signals of music and narration and a later described support program of physiological signal feedback recorded in voice track as DTMF signal; and a system controller 80 including an image/sound processing section 76 for processing the image signals and such voice signals as the music and narration from the deck 75, a pulse signal processing section 77 for processing the pulse signal from the sensor 73, a DTMF signal decoder 78 for decoding the DTMF signal from the deck 75, and a microcomputer 79 for controlling the respective sections 76, 77 and 78 for the signal processing.

Here, the video tape 74 constitutes an important element of the system employing the massager and stores in the image track a variety of images for providing to the user M relaxed feeling or refreshed feeling when the massager 71 is used in accordance with the steps of massage, in one of both side voice tracks (right channel, for example) such voice signals as the music and narration for providing to the user the relaxed or refreshed feeling in conformity to the image provided, and in the other side voice track (left channel, for example) the DTMF signal (tone signal) of the support program of physiological signal feedback control.

The support program of the physiological signal feedback control comprises a command for controlling the massager 71, a command for controlling the reproduction of the image and sound (voice) a command for controlling the head-mounted display 72, and a command for assigning the operation of the entire system.

The control of the massager 71 is to control the speed, strength, position and type of the massage performed, the control of the image and sound is to perform the fade-in, fade-out and ON/OFF of the image as well as volume adjustment of the music (or voice), the control of the head-mounted display 72 is ON and OFF control with respect to the power source, and the respective commands corresponding to these controls are to assign particular one of them.

The command for assigning the operation of the entire system is the one which selects one of certain number of the entire operation programs incorporated in the microcomputer 79 of the system controller 80, and the microcomputer 79 prepares a control signal for altering the operation of the massager with reference to this command and the pulse signal of the user M. The operation of the system in this embodiment shall be described next, with reference to an example of the support program of the physiological signal feedback control.

First, in the video tape 74, there are stored the images, musics (voices) and the support program of physiological signal feedback control, on the basis of a preliminarily supposed story of the operation control for the massager 71.

It is assumed here that the operation is of a program prepared as based on a story comprising a relax stage for relaxing the user (former part), a sleep stage for maintaining sleeping state when the user falls asleep (intermediate), and a refresh stage for awakening the user from the sleeping state (latter part). The video tape 74storing the support program of this story is loaded in the video deck 75 and replayed to place the system in its operating state. Then, the controller 80 takes up the image signal, voice signal of music or message and DTMF signal reproduced by the video deck 75, the image and voice signals are provided through the image/sound processing section 76 to the head-mounted type display 72 mounted onto the user's head, the DTMF signal is given to the DTMF signal decoder 78, and the command of the support program is decoded. When the command for controlling the head-mounted display 72 is the one showing "ON", the power source to the display 72 is made ON to have the display actuated, so that the image will be displayed on the display portion of the display 72, and the music, narration and the like voices are generated at the headphone portion. In this case, the microcomputer 79 causes the volume control and image-fading control to be performed at the image/sound processing section 76, on the basis of the command relating to the image and sound control provided by the DTMF signal.

The speed of the massage performed by the massager 71 is set by means of the command recorded in the video tape 74 for selecting the massaging speed. That is, a command of the support program of physiological signal feedback control for selecting either one of such three patterns for rendering the massaging speed of the massager 71 preliminarily set for the relax stage to be (1) of the same cycle as the pulse, (2) 95% of the pulse cycle and (3) 90% of the pulse cycle, is recorded on the video tape 74, and the microcomputer 79 selects one of these patterns on the basis of the command reproduced and decoded, prepares a control signal for controlling the massaging speed in correspondence to the pulse cycle obtained from the pulse signal processing section 77, and provides this control signal through the decoder 78 to the massager 71. A massaging drive of the massager 71 is, therefore, controlled to attain the massaging speed based on this control signal. Other adjustments than the massaging speed of the massager 71 are controlled as based on the other commands of the support program recorded in the video tape 74 as the DTMF signal. In an event where the heart rate decreases at a fixed ratio, the microcomputer 79 provides to the image/sound processing section 76 a command for reducing the volume of music (voice) and fading out the image. Here, a set value of the reducing ratio of the pulse and the reducing ratio of the volume of music (voice) are set by the command written by the DTMF signal in the video tape, and the microcomputer 79 of the system controller 80 discriminates the set value of the reducing ratio of the pulse and the reducing ratio of the music (voice), on the basis: of this command.

In correspondence to the next sleep stage, there are written in the video tape 74 commands for rendering the massaging speed of the massager 71 to be of the same cycle as the pulse, the massaging strength to be weaker and the music (voice) volume to be smaller, so that the sleep of the user M will not be hindered, and the microcomputer 79 of the system cotroller 80 performs the corresponding control process on the basis of these commands decoded by the decoder 78. That is, the command for the volume control is sent to the image/sound processing section 76, whereas the control signal for controlling the massaging strength and speed is sent through the decoder 78 to the massager 71 for operating the massager 71 at the controlled strength and speed of the massaging.

Further, in correspondence to the next refresh stage, there are recorded in the video tape 74 commands of the support program of physiological signal feedback control for selecting either one of such three patterns for rendering the massaging speed of the massager 71 to be, for example, (1) of the same cycle as the pulse, (2) 105% of the pulse cycle, and (3) 110% of the pulse cycle, and the microcomputer 79 of the system control 80 selects the pattern on the basis of the command decoded by the decoder 78, and provides to the massager 71 a control signal for controlling the massaging speed of the massager 71 on the basis of the pulse cycle extracted at the pulse signal processing section 77, to set a massaging speed suitable for the refreshing.

In respect of such items as the strangth, type, position and so on of the massaging, too, there are recorded in the video tape 74 respectively corresponding commands by means of the DTMF signal, for rendering an operation of the massager 71 suitable for the refresh stage to be obtainable. Therefore, the microcomputer 79 of the system controller 80 is to perform the control processing for these items, too.

While the foregoing embodiment relates to the system for controlling the massager 71 and the video tape 74 employed as the storage medium, it should be appreciated that the embodiment is employable in respect of any device including game or playing machines which performs a control with the physiological signal subjected to the feedback.

Further, while in the foregoing embodiment the video tape is employed as the storage medium, any of such other storage medium as video CD, DVD, LD and so on in which the images and music (voice) can be stored together may also be employed. Further, CDROM and semiconductor memory may also be used. While the command is recorded by means of the voice signal comprising the DTMF signal, the command may also be recorded by such signal modified by an audible frequency, as the so-called modem signal.

Figure 6:
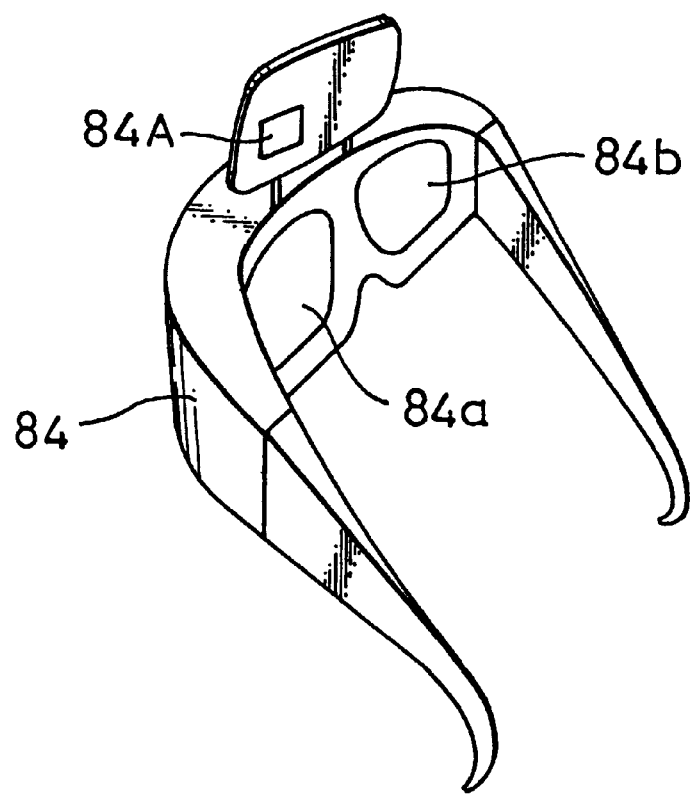
FIG. 6 is a schematic perspective view of the display device in still another embodiment of the present invention.

FIG. 6 shows a head-mounted display device 84 in another embodiment of the present invention, in which a bone-conducting voice vibration detecting section 84A for detecting the bone conducting voice vibration is provided for engaging with the forehead of the user when the display device 84 is mounted on the user's head.

Referring further to the above with reference also to FIG. 7, there is provided a voice recognition system 90 which comprises a bone-conducting voice vibration detecting means 91 in the bone-conducting voice vibration detecting section 84A, an amplifier means 92, and a signal recognizing means 93. As the user speaks, the bone-conducting voice vibration detecting means 91 detects the bone-conducting voice vibration propagated through the user's skull and outputs detected signal as amplified. Next, the amplifier means 92 further amplifies the output signal from the bone-conducting vibration detecting means 91 and provides an output signal through, if required, a filtering process.

At the signal recognizing means 93, the output signal from the amplifier means 92 is subjected to a judgement, to which one of signal patterns preliminarily registered the output signal corresponds. In order to elevate the recognition rate of the signal recognizing means 93, the display device is arranged for allowing the bone-conducting voice vibration detecting means 91 to be engaged with a proper position around an eyebrow or a proper position between the eyebrow and top edge of the forehead.

Figure 8:
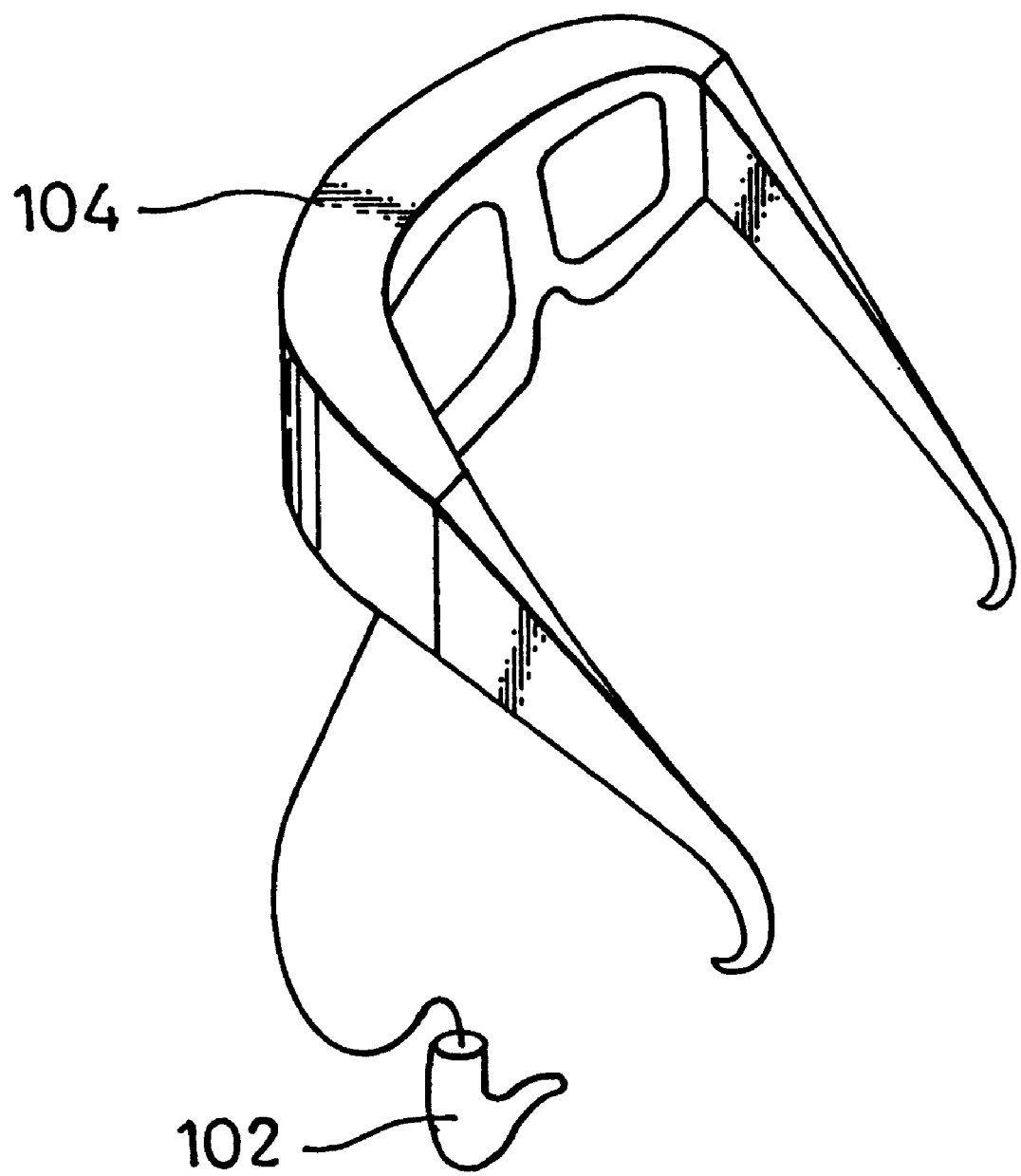
FIG. 8 is a perspective view of the display device used in still another embodiment of the present invention.

As an aspect of the bone-conducting voice vibration detecting means 91, on the other hand, it is also possible to employ such ear-mounting piece 102 as shown in FIG. 8, as connected to a head-mounted display device 104, the ear-mounting piece 102 being formed to be inserted into the auditory canal of the user's ear, or even one which detects the bone conducting vibration at a part adjacent to ear, concha or part of concha. While in the above only the bone-conducting voice vibration detecting means 91 is referred to as provided to the display device 84, it may be possible to further provide the amplifier means 92 to the device 84 in addition to the detecting means 91.

In another embodiment shown in FIG. 9 of the present invention, an arrangement is made to tightly combine the foregoing embodiment of FIGS. 1 and 2 with the embodiment of FIGS. 6 and 7. In this case, in particular, a chair system 95A is additionally connected to a recognition control means 94A connected to the signal recognizing means 93A, to which system such function as an input interface is provided.

Referring to the present embodiment with reference also to FIG. 2, the user actuates the control device 12 with the start button 22G pushed, mounts the display device 14 to the head and sits on the massager 10.

The pushed state of the start button 22G sent to the system control section 22A, and this section 22A executes the control causing, through the image/sound control section 22E, the video CD driving section 23 to reproduce the moving image track in which the modem signal is recorded in the voice range. From the codes of the modem signal reproduced with this control, the control data are decoded at the modem signal decoding section 22F, the decoded control data are sent to the system control section 22A, and the data groups (for example, the foregoing five data of (1) to (5)) in the respective moving picture tracks of the track Nos. A to E are read in the system control section 22A immediately after actuation of the device, thereafter a menu picture is displayed on the image display sections 14a and 14b, and the user can perform the course selection, its confirmation and chair system start by speaking the course selection, comfirmation and start as instructed in the menu picture.

Provided that two courses of "1. Midsummer Sun" and "2. Morning Glow" are prepared for the course, and that the user can select, as experience time, one of "1. 10 minutes" and "2. 15 minutes", the chair system is to be started after the selection of one experience time.

The user in the state of mounting the display device 104 on the head watches such menu picture as in FIG. 10A, and tells "one" if the course "1. Midsummer Sun" is desired, for example. When the menu picture displays the figure "1" to indicate a judgement that the course 1 has been selected, the user tells "definite", then such menu picture as FIG. 10B is shown, the user tells "one" if a course "1. 10 minutes" is intended, for example, the picture displays "1" to show the judgement of the selection to be the course 1, then the user tells "start", whereby the system is to be started. In this case, necessarily, such voice signals as "one", "two", "definite" and "start" or patterns of their bone-conducting voice signals are preliminarily registered in the signal recognizing means 93, which carries out a pattern matching every time when signals are input. At the recognition control means 94A, the present system status is grasped by means of system status information from the chair system 95A and the history of the control signals so far output, and a new control signal is provided to the chair system 95A depending on the recognition signal received.

While in the present embodiment an application to the chair system 95A has been described, it should be appreciated that the voice recognition system 90 in the embodiment shown in FIGS. 6 and 7 can be employed as an interface between the user and a certain system or, in the case where the head-mounted display device 104 is employed, an input interface between the user and the system, and that its effect is remarkable.

What is claimed is:

1. A relax refresh system comprising:
   detecting means for detecting a physiological state of a user and outputting a detection signal;
   a recording medium including recording zones respectively for recording image signals and sound signals including music signals and narration signals in a manner of allowing reproduction of the image signals and the sound signals through a random access;
   a recording medium driving means for driving the medium to take desired ones of the image signals and the sound signals out of the recording medium;
   an image reproducing means connected to the recording medium driving means for reproducing the image signals;
   a sound reproducing means connected to the recording medium driving means for reproducing at least one of the music signals and the narration signals of the sound signals;
   a massager disposed in contact with a body of the user for selectively performing a first massage operation for relieving physical fatigue, and a second massage operation for physically awakening the user;
   a control section comprised of first, second and third control means, the first control means controlling the recording medium driving means so as to modify a recorded position on the recording medium to select respective signals to be reproduced to meet an operation course preliminarily selected by the user from a plurality of pre-established relax refresh operation courses in view of the state of the user grasped on the basis of the detection signal of the physiological state detecting means, for reproducing at the image reproducing means and sound reproducing means the image signals and the sound signals output from the recording medium driving means and for performing one of a stopping of both of the sound reproducing means and the image reproducing means in view of the detected physiological state of the user and a controlling of the recording medium driving means to change the images and sounds in response to changes in the detected physiological state of the user, the pre-established courses comprising images only, images plus music, images plus narration, images plus music and narration, and sound only, the second control means selecting respective narration signals to produce a narration conforming to a state of the user grasped on the basis of the detection signal of the detection means and for reproducing at the sound reproducing means the narration signals of the selected narration, and the third control means receiving the detection signal from the physiological state detecting means to judge and grasp the state of the user for controlling the massager to have the first and second massage operations executed respectively along the relax refresh operation course selected on the basis of the judged state of the user; and a head-mounted member incorporating at least the detecting means, the image reproducing means and sound reproducing means and, when the member is mounted to the head of the user, positioning the image reproducing means proximately in front of eyes of the user for displaying the image of the selected operation course under the control of the first control means, and positioning the sound reproducing means proximately to ears of the user for reproducing the sounds of the selected operation course under the control of the first control means and the selected narration under the control of the second control means.

2. The system according to claim 1 wherein the physiological detecting means comprises eye state detecting means for detecting eyeblinking and eye opening/closing action of the user's eyes, and means for processing signals from the eye state detecting means; and the head-mounted member further incorporating the eye state detecting means and the signal processing means along with both of the image and sound reproducing means.

3. The system according to claim 1 wherein the recording medium includes control data for the first, second and third control means, the control data recorded by means of modem signal in the form of an analog signal in audible band as written in the recording zone, and the control section further comprising a decoding means connected to the recording medium driving means for decoding the modem signal from the recording medium driving means to control at least one of the first, second and third control means in accordance with the control data of the decoded modem signal.

4. The system according to claim 1 wherein there is recorded in every recording zone of the recording medium a plurality of control data for enabling the first, second and third control means to control the recording medium driving means, the image reproducing means, the sound reproducing means and the massager along the operation course preliminarily set to meet the physiological state of the user, and allocation data for the type of image and sound, and continuing time data for the respective data.

5. The system according to claim 1 wherein the recording medium comprises a video CD.

* * * * *